United States Patent
Fridman et al.

(12)

(10) Patent No.: US 6,316,554 B1
(45) Date of Patent: Nov. 13, 2001

(54) PROCESS FOR THE PRODUCTION OF WATER-ABSORBING COMPOSITIONS

(75) Inventors: Israel D. Fridman, Belmont, MA (US); John C. Lamont; Ervin Dan, both of Calgary (CA)

(73) Assignee: Camelot Superabsorbents Limited, Calgary (CA)

( * ) Notice: Subject to any disclaimer, the term of this patent is extended or adjusted under 35 U.S.C. 154(b) by 0 days.

(21) Appl. No.: 09/011,538
(22) PCT Filed: Aug. 9, 1996
(86) PCT No.: PCT/EP96/03539
  § 371 Date: Sep. 28, 1998
  § 102(e) Date: Sep. 28, 1998
(87) PCT Pub. No.: WO97/06191
  PCT Pub. Date: Feb. 20, 1997

(30) Foreign Application Priority Data

Aug. 10, 1995 (GB) .................................................. 9516399

(51) Int. Cl.$^7$ ....................................................... C08F 2/14
(52) U.S. Cl. .............................. 526/89; 526/271; 526/272
(58) Field of Search ............................. 526/89, 271, 272

(56) References Cited

U.S. PATENT DOCUMENTS

| | | | | |
|---|---|---|---|---|
| 3,558,570 | * | 1/1971 | Rinno et al. | 526/89 |
| 3,940,351 | * | 2/1976 | Schlatzer, Jr. | 526/89 |
| 4,923,940 | * | 5/1990 | Hsu | 526/208 |
| 5,684,090 | * | 11/1997 | Chupka, Jr. | 525/285 |

* cited by examiner

Primary Examiner—Bernard Lipman
(74) Attorney, Agent, or Firm—Hodgson Russ LLP

(57) ABSTRACT

A process for producing a copolymer of an a, β-unsaturated monormer having at least one pendant unit selected from a carboxylic acid group and derivatives thereof, and a copolymersable monomer is described in which the process is carried out in a single solvent which is particularly an aromatic solvent. Processes of controlling the reaction and the particle size of the polymer produced are also described.

6 Claims, No Drawings

PROCESS FOR THE PRODUCTION OF WATER-ABSORBING COMPOSITIONS

The present invention relates to a process for producing water-absorbing compositions of the kind sometimes known as superabsorbent polymers.

Water-absorbing compositions are widely used in the manufacture of products which require high absorption capability; for example, surgical and dental sponges, tampons, sanitary napkins and pads, pant liners, disposable diapers, adult incontinence pads, coverstock for feminine hygiene products, training pads, bandages, wound covers, patient underpads (for example pads of the type described in U.S. Pat. Nos. 3,814,101 4,342,314 and EP 0 052 403 which are incorporated herein by reference), mortuary pads, casket liners, forensic examination pads, meat trays, soaker pads for food use, medical tray pads, fenestration drapes, other medical or surgical related articles, seed germination pads, capillary mats, baby bibs, desiccant strips for anti-rust use, bath mats, packaging, sorbents, clothing, breast pads, underarm pads, industrial wipes, domestic wipes, wipes, filters, cable wrap, food preservation articles, roofing materials, automotive trim, furniture, gasket sealants, pond liners, bedding, cement, household pet litter, soil modifiers, and the like. Water-absorbing compositions are also used for the modification of soil to improve water retention and increase air capacity and for a host of other applications. It will be understood that some of the articles referred to are not per se absorbent but may be rendered absorbent by means of the presence in their structure, or at their surface of absorbent materials.

Water-absorbent compositions suitable for these and other uses may be in any suitable form including powders, fibers, filaments, films and coatings on fibers, filaments, sheets and fabrics.

As used herein, the term "water" when used in the phrases "water-absorbing", "water-absorbent", "water-swellable" and the like is understood to mean not only water but also aqueous media such as, in particular, electrolyte solutions such as body fluids and other polar organic liquids.

Water-absorbent compositions may be produced from a variety of polymers. One class of water-absorbent compositions are those produced from a copolymer of an $\alpha,\beta$ unsaturated monomer having at least one pendant unit selected from a carboxylic acid group and derivatives thereof and a copolymerizable monomer. A proportion of the pendant units are present in the final copolymer as the free acid and a proportion as the salt of the acid. These copolymers are capable of being cross-linked, either internally or with a variety of cross-linking agents, to form the water-swellable composition. Examples of water-absorbent compositions of this type can be found in U.S. Pat. Nos. 4,616,063, 4,705,773, 4,731,067, 4,743,244, 4,788,237, 4,813,945, 4,880,868 and 4,892,533 and European Patent Nos. 0 272 074 and 0 264 208, European Published Application Nos. 0 436 514, 0 269 393, 0 397 410, and 0 232 121 and United Kingdom Patent No. 1 288 563. Other water-absorbent compositions are described in WO93/12275 and WO93/17066. Each of these documents are incorporated herein by reference.

Suitable derivatives of carboxylic acid groups include carboxylic acid salt groups, carboxylic acid amide groups, carboxylic acid imide groups, carboxylic acid anhydride groups and carboxylic acid ester groups.

Suitable $\alpha,\beta$ unsaturated monomers having at least one pendant unit selected from a carboxylic acid group and derivatives thereof include maleic anhydride; crotonic acid; fumaric acid; mesaconic acid; the sodium salt of maleic acid; the sodium salt of 2-methyl, 2-butene dicarboxylic acid; the sodium salt of itaconic acid; maleamic acid; maleamide; N-phenyl maleimide; maleimide; maleic anhydride; fumaric anhydride; itaconic anhydride; citraconic anhydride; mesaconic anhydride; methyl itaconic anhydride; ethyl maleic anhydride; diethylmaleate; methylmaleate and their mixtures.

Any suitable copolymerizable comonomer can be employed. Suitable copolymerizable comonomers include ethylene, propylene, isobutylene, $C_1$ to $C_4$ alkyl methacrylates, vinyl acetate, methyl vinyl ether, isobutyl vinyl ether, and styrenic compounds having the formula:

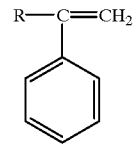

wherein R represents hydrogen or an alkyl group having from 1 to 6 carbon atoms and wherein the benzene ring may be substituted. Suitable substituents include low molecular weight alkyl or hydroxy groups.

Suitable $C_1$ to $C_4$ alkyl acrylates include methyl acrylate, ethyl acrylate, isopropyl acrylate, n-propyl acrylate, n-butyl acrylate and the like and their mixtures.

Suitable $C_1$ to $C_4$ alkyl methacrylates include methyl methacrylate, ethyl methacrylate, isopropyl methacrylate, n-propylmethacrylate, n-butyl methacrylate, and the like, and their mixtures.

Suitable styrenic compounds include styrene, $\alpha$-methylstyrene, p-methylstyrene, t-butyl styrene and their mixtures.

The pendant units on the $\alpha,\beta$-unsaturated monomer will determine what, if any, additional reactions must be carried out to obtain a copolymer in which a proportion of the pendant units are present as the free acid and a proportion are present as the salt of the acid.

In general, if the $\alpha,\beta$-unsaturated monomer bears only carboxylic acid amide, carboxylic acid imide, carboxylic acid anhydride, carboxylic acid ester groups, or mixtures thereof, it is necessary to convert at least a portion of these carboxylic acid derivative groups to carboxylic acid groups by, for example, an hydrolysis reaction. If the $\alpha,\beta$-unsaturated monomer bears only carboxylic acid salt groups, partial acidification to form carboxylic acid groups will be necessary.

One copolymer that is particularly suitable for use in the production of water-absorbing composition is a copolymer of maleic anhydride and isobutylene. Another suitable copolymer is that of maleic anhydride and styrene copolymer. Suitable copolymers will preferably have peak molecular weights of from about 5,000 to about 500,000 or more.

Suitable copolymers of maleic anhydride and isobutylene can be prepared using any suitable conventional method. Such copolymers are also commercially available from Kuraray Isoprenc Chemical Company, Ltd., Tokyo, Japan, under the trade mark ISOBAM. ISOBAM copolymers are available in several grades which are differentiated by viscosity molecular weight: ISOBAM-10, 160,000 to 170,000; ISOBAM-06, 80,000 to 90,000; ISOBAM-04, 55,000 to 65,000; and ISOBAM-600, 6,000 to 10,000.

The copolymer of the $\alpha,\beta$-unsaturated monomer described above and the copolymerisable monomer may be combined with a cross-linking agent having two or more groups reactive with functional groups on the polymer chain, for example hydroxyl or heterocyclic carbonate groups. In one alternative, it may crosslink intramolecularly in the absence of an external cross-linking agent by means of covalent or hydrogen bonds.

The water-absorbent composition preferably comprises from about 20 to about 80 wt % pendant carboxylic acid groups and from about 80 to about 20 wt % pendant carboxylate salts and a suitable amount of a cross-linker if required.

Any suitable free radical polymerization catalyst can be used to catalyze the polymerization reaction. Suitable catalysts include benzoyl peroxide, such as that sold under the trade name PERKADOX and the VAZO azobisisobutyronitrile catalysts which are commercially available from E. I. DuPont de Nemours. VAZO-64 and VAZO-67 catalysts are suitable for use in this invention at amounts of from about 0.2 to about 2 mole percent or greater based on the amount of $\alpha,\beta$ unsaturated monomer such as maleic anhydride.

The water-absorbing composition of this invention can be prepared using any suitable blending method. After the water-absorbing composition is prepared, but typically before it is cured, but in some instances as it is curing, it is processed into any desired form using conventional methods of fabrication. For example, the water-absorbing composition can be subjected to casting; spray drying; air-assisted spray drying; air attenuation; or wet, dry or flash spinning. In addition, the water-absorbent composition may be a coating on a substrate. The coating may be continuous or may be discontinuous. The selection of the process is typically dictated by the shape or form needed for the designated end use.

The water-absorbing composition may be fabricated into any suitable form including films or sheets, powders and granules, fibers and any form into which fibers can be processed such as for example milled fibers, chopped fibers, fluff or bulk fibers, strands, yarns, woven fabrics and non-woven mats. Fabrication may take place using a variety of methods, including twisting, beaming, slashing, warping, quilling, severing, texturizing, weaving, knitting, braiding.

The water-absorbing composition may also be used to coat fibers, filaments, sheets or fabrics as described in co-pending application number U.S. Ser. No. 081337,291 which is incorporated herein by reference.

Irrespective of which method is chosen for the preparation of the copolymer, it is necessary to have the various monomers in solution. However, in the past it has been difficult to provide a solvent system that dissolves all of the monomers and the polymerisation initiator but does not dissolve nor swell the polymer. Thus, conventionally a mixed solvent system has to be used.

Solvents currently used as part of a solvent system for use in the preparation of the copolymer include esters of acetic acid, formic acid, and propionic acid and mixtures of the resulting acetates, formates, and propionates.

Specific examples of known solvent systems are those including ethyl acetate, isopropyl acetate, ethyl formate, butyl formate, ethyl propionate, and their mixtures. A particularly preferred known reaction solvent includes isopropyl acetate.

The polymerisation reaction solvent may be blended with a $C_6$ to $C_{12}$ hydrocarbon diluent to facilitate removal of the reaction solvent and any unreacted $\alpha,\beta$ unsaturated monomer by distillation after the polymerisation reaction has been completed. The amount of hydrocarbon diluent added can vary over a wide range of from about 10 to about 75 weight percent of the total blend of reaction solvent and diluent.

The diluent can be used over a wide range of concentrations. However, it is important that is not employed in an amount which significantly affects the solubility of the monomers in the reaction solvent/diluent blend. Particularly suitable $C_6$ to $C_2$ hydrocarbon diluents are the $C_6$ to $C_2$ aliphatic hydrocarbons including hexane, heptane, octane, nonane, decane, undecane, dodecane, and their isomers and mixtures. One known blend of reaction solvent and diluent is isopropyl acetate and either octane or decanes. A particular known solvent is that sold under the trade name ISOPAR G which is believed to be a mixture of isopropyl acetate and undecanes.

However these known solvent systems have certain disadvantages and drawbacks, one of which is that these solvents have a tendency to swell the polymer which is disadvantageous as the polymer is then difficult to handle during any subsequent processing steps.

We have now discovered that the problems associated with known solvent systems are overcome if the reaction is carried out in a single solvent which is selected such that the monomers and initiator are soluble in the solvent, the polymer is insoluble in the solvent and the solvent does not swell the resultant polymer. We have further discovered that a particularly suitable solvent is an aromatic solvent. Suitable aromatic solvents include benzene and substituted benzenes such as toluene or xylene, with toluene being particularly preferred.

Thus, according to a first aspect of the present invention there is provided a process for producing a copolymer of an $\alpha,\beta$-unsaturated monomer having at least one pendant unit selected from a carboxylic acid group and derivatives thereof, and a copolymerisable monomer comprising the steps of copolymerizing the monomers in solution in a single solvent. The solvent is preferably an aromatic solvent. Suitable solvents include benzene and substituted benzenes such as toluene or xylene, with toluene being particularly preferred.

These solvents are particularly suitable as solvents for the reaction as both the $\alpha,\beta$-unsaturated monomer and the copolymerisable monomers used in the production of water-absorbent composition of the described type, are soluble in the aromatic solvents as is a wide range of polymerisation initiators. In addition, the resultant copolymer is not soluble in these solvents. Further, these solvents do not cause the resultant copolymer to swell and do not result in a sticky polymer. Thus, further processing of the copolymer to provide the water-absorbent composition is facilitated. An additional advantage is that if the $\alpha,\beta$-unsaturated monomer is an anhydride, and the solvent is an aromatic solvent, the anhydride group will not be hydrolysed.

In addition to the single solvent system described above, we have discovered that various advantages may be obtained by adding an amount of aromatic solvent to a conventional solvent system. In particular, the aromatic solvent will, on addition to the solvent system, solubilise components not readily soluble in the conventional solvents and/or reduce the stickiness of the resultant copolymer.

Once the copolymer is formed, the second step in the production of the water-absorbing composition is the, at least partial, neutralization of the copolymer. The degree of partial neutralization is preferably in the range of from about 0.3 to about 0.9 and preferably from about 0.5 to about 0.86.

Where the solvents of the present invention are used for the reaction, and the solvent is, or includes an aromatic solvent neutralization may be carried out before or after the aromatic solvent is removed or while the aromatic solvent is being removed. Neutralization may be carried out using any suitable neutralization agent. The preferred neutralization agent is an aqueous solution of sodium hydroxide.

Thus, according to a second aspect of the present invention there is provided a process for producing a water-absorbent composition comprising the steps of producing a copolymer of an α,β-unsaturated monomer having at least one pendant unit selected from a carboxylic acid group and derivatives thereof, and a copolymerisable monomer in accordance with the process of the above first aspect wherein the solvent is an aromatic solvent, partially neutralizing at least a portion of the carboxylic acid groups; and allowing the resultant copolymer to cure. An external cross-linking agent may be present to crosslink the copolymer.

The neutralization step may be carried out by any suitable means. One suitable process is to separate the copolymer from the reaction mixture by filtration and then drive off the aromatic solvent to leave a dry powder. This is then dissolved in an aqueous solution of the neutralization agent such that the copolymer is partially neutralised. A preferred method is to form a dilute solution of the copolymer in the solution of the neutralization agent and subsequently concentrate it to the concentration of solids content required for further fabrication.

One alternative process is to add the aqueous solution of the neutralization agent to the slurry of the copolymer in the aromatic solvent and then remove the aromatic solvent by distillation. The aromatic solvent will distil off in an azeotrope-like manner. Hydrolysis occurs as the aromatic solvent is removed and the concentration of the solution increases. The resultant liquid is added to water before being concentrated to form a syrup which can then be fabricated by any suitable method.

A second alternative process is to inject steam into the slurry of the polymer in the organic solvent. The injection of steam raises the temperature such that the aromatic solvent boils such that the solvent, together with water, distils in an azeotrope-like manner. Hydrolysis will occur simultaneously. The neutralization agent is added at any convenient point.

A third alternative process is to add the aqueous solution of the neutralization agent to the slurry of the copolymer in the aromatic solvent, a phase separation can then be carried out as the hydrolysed polymer will be found in the lower aqueous layer. The aqueous solution of the hydrolysed polymer is then concentrated, this concentration removes the last traces of aromatic solvent. The organic layer from the phase separation may be dried and recycled.

Curing is preferably achieved by reaction with an external crosslinker for the copolymer.

According to a third aspect of the present invention there is provided a solution of an α,β-unsaturated monomer having at least one pendant unit selected from a carboxylic acid group and derivatives thereof, and a copolymerisable monomer in a solvent comprising an aromatic solvent. Suitable solvents include benzene and substituted benzenes such as toluene or xylene, with toluene being particularly preferred.

Whether the reaction of the α, β-unsaturated monomer with the copolymerisable monomer is carried out in a solvent comprising an aromatic solvent or in one of the known solvent systems, there are a variety of problems associated with the reaction process. In particular, the reaction may become very hot due to the heat generated by the reaction. This means that the reaction can be difficult to control and the process cannot readily be operated continuously throughout the batch process nor can it be operated continuously.

We have now discovered that these problems can be overcome by one or more of: controlling the addition rate of the monomers to the reaction vessel; allowing evaporative cooling to occur within the reaction vessel; controlling the concentration and temperature of the feed to the reaction vessel; using the heat of the reaction to heat incoming reactants to reaction temperature; or precharging a seed amount of at least one of the monomers to the reaction vessel.

Thus, according to a fourth aspect of the present invention there is provided a process for producing a copolymer of an α,β-unsaturated monomer having at least one pendant unit selected from a carboxylic acid group and derivatives thereof, with a copolymerisable monomer comprising reacting the α, β-unsaturated monomer with the copolymerisable monomer in a reaction vessel and controlling the reaction temperature by one or more of:

(A) controlling the addition rate of at least one of the reaction components, including the solvent; and preferably of one or more of the monomers;

(B) allowing evaporative cooling to occur within the reaction vessel;

(C) controlling the concentration and temperature of the feed to the reaction vessel;

(D) using the heat of the reaction to heat incoming reactants to reaction temperature; and (E) precharging a seed amount of at least one of the monomers to the reaction vessel.

The reaction is preferably operated in a semi-batch mode by which is meant feeding one or more of the monomers to the batch-reaction vessel at a controlled rate during polymerisation. Solvent, monomer(s) and initiator are all fed to the reaction vessel.

A further problem associated with some prior art methods for producing a copolymer of an α,β-unsaturated monomer having at least one pendant unit selected from a carboxylic acid group and derivatives thereof, with a copolymerisable monomer is that the resultant polymer may be formed having a small particle size. This is a disadvantage because a slurry comprising the copolymer will have a high viscosity and is therefore difficult to handle. Thus it would be advantageous to be able to increase the particle size of the polymer.

We have now discovered that by controlling the feed rate of the monomer to the reaction, the particle size of the resultant polymer may be controlled.

Thus, according to a fifth aspect of the present invention there is provided a method of controlling the particle size of the polymer produced in the reaction of a copolymer of an α,β-unsaturated monomer having at least one pendant unit selected from a carboxylic acid group and derivatives thereof, with a copolymerisable monomer comprising reacting the α,β-unsaturated monomer with the copolymerisable monomer in a reaction vessel and controlling the addition rate of at least one of the reaction components.

By the method of this aspect of the invention, a copolymer having larger particle size than has been available heretofore can be achieved and thus the viscosity of the resultant slurry is reduced. A further benefit of being able to increase the particle size of the polymer is that for a given viscosity, a higher concentration of solids can be present in the solvent. Thus where a process is capable of handling a certain viscosity of slurry, more solids can be handled for the same viscosity and thus efficiency can be increased.

Particular embodiments of the present invention will now be described with reference to the following examples:

EXAMPLE 1

A solution of maleic anhydride in toluene was prepared and held in an agitation tank fitted with a feed metering system at a temperature of from 20 to 30° C. A 10% solution of benzoyl peroxide was prepared and the water was decanted. The benzoyl peroxide solution was added to the maleic anhydride solution and the vessel was then thoroughly de-aerated with nitrogen sparging. A small amount of benzoyl peroxide acted to assist with the removal of oxygen from the vessel.

The solution of maleic anhydride may have a concentration of <10 to 99%. Alternatively, molten maleic anhydride may be used.

A jacketed pressure vessel (75 to 100 psig) equipped with agitation means (a minimum of two AFT impellers, 0.3<LD>0.95) was prepared by charging sufficient toluene into the reactor to cover the bottom impeller. Thus, sufficient toluene was added to provide the necessary priming for agitation. A portion of the benzoyl peroxide solution was added to the reactor and the system was air-purged to attain strict anhydrous conditions. This was accomplished by repeated vacuum and nitrogen pressure flushes, or by repeated nitrogen pressure and venting cycles to atmospheric pressure. As benzoyl peroxide may react with the toluene at this stage, a small quantity of isobutylene was introduced into the vessel. A small quantity of maleic anhydride was also added.

The reactor was heated to the selected initial reaction temperature, which was typically 75 to 100° C. During heatup the reactor contents were thoroughly de-aerated with nitrogen sparging. When the reactor had reached the target temperature, a specific amount of isobutylene was added to provide a given initial stoichiometric excess.

Once the reactor was stable at the chosen temperature, the two feeds were started simultaneously. The maleic anhydride feed was filtered to recover traces of maleic acid. The isobutylene was delivered from a pressurized cylinder. Typical feed durations were between 60 and 180 minutes, depending on equipment characteristics and cooling capability. The molar ratio of isobutylene: maleic anhydride in the feed was preferably 2:1.

The onset of reaction was evidenced by the appearance of solid matter in the reactor contents. Thus a change in appearance from clear and transparent prior to reaction, to opaque and milky when the reaction was in progress was noted. The start of the reaction was also evidenced by a slight increase in temperature and a slight decrease in pressure.

Where the size of the reaction vessel is small, the reaction temperature may be controlled using the vessel's jacket. However, when the reactor is large, the jacket cannot effectively control the reaction temperature and thereby the reaction rate and thus, the addition of feed may be used to moderate the heat of the reaction.

In particular, it is desirous to retain the reaction mixture in the region of 80° C. When the heat of the reaction mixture rises due to the heat generated by the reaction, cold reactants, cold solvent or both cold reactants and cold solvent can be introduced into the vessel; the heat generated by the reaction being utilized to bring the cool reactants and/or solvent to the reaction temperature.

As more feed was added, the reactor pressure increased and reached a maximum of 25–35 psig due to the build-up of excess isobutylene. The batch underwent an increase in solids content with increased polymer content, and vigorous agitation was necessary to maintain the suspension quality. The ability to agitate the reaction mixture also changes.

At the end of the feed period, the temperature was increased to 85° C. and held for 1 hour to react the last remaining traces of maleic anhydride.

At the end of the reaction period, the isobutylene excess was vented out and recovered for subsequent use, or disposed of by incineration.

With the reactor at atmospheric pressure and open to an overhead condenser, the required amount of water and sodium hydroxide (NaOH) were then added. This addition took place all at once, although it can be added in a step-wise manner.

Heat was applied to the reactor through the jacket, and a constant boiling condition was reached at 84° C. at atmospheric pressure. The toluene/water constant boiling point mixture was recovered by condensation with a constant volumetric composition ratio of about 84/16. As the reactor mixture became toluene-poor, the condensate composition began drifting until only water was collected, and the boiling point began to climb towards that of water.

In an alternative method, direct stream stripping of the polymer/toluene slurry can be carried out to reduce the stripping and neutralization cycle time by avoiding the slow heat transfer through the reactor jacket. Mass balance showed that the amount of steam required for stripping energy is less than the water required in the final solution.

The recovered toluene/water mixture can be separated by decantation. The water portion can be reused in subsequent stripping passes without any treatment. The toluene portion may need further drying before it can be reused in the anhydrous polymerization step.

At the end of the distillation process—whether by boiling or direct steam stripping—the material was heated under pressure to ca. 135° C. and held for about 3 hours with agitation to complete the polymer solution process. The aqueous polymer solution was subsequently cooled down to 75–85° C. and any post-additives are added.

The polymer solution was then filtered and packed.

Details of the experiment are summarised in the Tables 1 to 3:

TABLE 1

| Polymerization | Composition per 100 parts of Maleic Anhydride | % of Slurry | % of Total | % of Polymer |
| --- | --- | --- | --- | --- |
| Toluene | 779.33 | 78.79 | 47.94 | 392.49 |
| Maleic anhydride | 100.00 | 10.11 | 6.15 | 50.36 |
| Isobutylene | 109.34 | 11.05 | 6.73 | 55.07 |
| Benzoyl peroxide | 0.50 | 0.051 | 0.031 | 0.252 |
| Total Slurry solids 16.8% | 989.17 | 100.00 | 60.85 | 498.17 |

TABLE 2

| Neutralization | Composition per 100 parts of Maleic Anhydride | % of Slurry | % of Total | % of Polymer |
|---|---|---|---|---|
| NaOH (50%) | 81.63 | 8.25 | 5.02 | 41.10 |
| $H_2O$ | 554.87 | 56.09 | 34.13 | 279.44 |
| Subtotal solids 25.0% | 1,625.67 | 164.35 | 100.00 | 818.73 |

TABLE 3

| | Composition per 100 parts of Maleic Anhydride | % of Slurry | % of Total | % of Polymer |
|---|---|---|---|---|
| Polymer (pre-neutralization) | 157.74 | 15.95 | 9.70 | 97.44 |
| Polymer (post-neutralization) | 198.56 | 20.07 | 12.21 | 100.00 |

EXAMPLES 2–19

Experiments were carried out to illustrate the various aspects of controlling the temperature of the reaction in accordance with the present invention. The details of the experimental procedures and the results obtained are set out in Table 4.

TABLE 4

| Ex No | Demonstration Type | A | B | C | Solvent Type | Polymerisation Process Type | D | Solvent Removal Process | E | Concentration Process | F |
|---|---|---|---|---|---|---|---|---|---|---|---|
| 2 | AIBN.iPAc/isopar solvent pair. Batch process | AIBN | 2.0 | 64–66 | iPAc/isopar | Batch | 100/100/100 | iPAc distillation. Filtration to isopar wet cake. Vacuum oven drying | | | |
| 3 | BPO.iPAc/isopar solvent pair. Batch process | BPO | 2.0 | 75–85 | iPAc/isopar | Batch | 100/100/100 | iPAc distillation. Filtration to isopar wet cake. Vacuum oven drying | | | |
| 4 | BPO. Toluene. Batch process. Toluene distillation | BPO | 0.5 | 79–92 | Toluene | Batch | 100/100/100 | Toluene/water azeotrope distillation to 25% syrup | 50.0 | | |
| 5 | Feed process. Filtration to wet cake | BPO | 0.5 | 79–91 | Toluene | 90 min feed: tol/Man and $iC_4$ | 20/4.8/0 | Filtration to toluene wet cake | | | |
| 6 | Improved control with longer feed process | BPO | 0.5 | 77–79 | Toluene | 140 min feed: tol/Man and $iC_4$ | 20/4.8/0 | Filtration to toluene wet cake | | | |
| 7 | Improved control with higher seeding of monomers/BPO. Toluene decantation. Evaporation | BPO | 0.5 | 82–85 | Toluene | 140 min feed: tol/Man and $iC_4$ | 25/12.5/2.2 | Partial toluene decantation. Toluene/water distillation | 49.0 | Atm. evaporation in open vessels | 2.0/3.0 |
| 8 | Toluene displacement by direct steam injection/stripping Recycled tol/$iC_4$ | BPO | 0.5 | 82–84 | Toluene | 140 min feed: tol/MAn and $iC_4$ | 50/12.5/2.2 | Direct steam injection/stripping to 28% | 47.5 | Atm. evaporation in open vessels | 2.0/3.0 |
| 9 | Toluene displacement by conventional distillation. Recycled tol/$iC_4$ | BPO | 0.5 | 81–85 | Toluene | 140 min feed: tol/MAn and $iC_4$. Recycled tol/$iC_4$ | 50/12.5/2.2 | Batch toluene/water distillation | 45.0 | Atm. evaporation in open vessels | 2.0/3.0 |
| 10 | Semi-commercial scale drying to powder. Powder neutralized to Syrup | BPO | 0.5 | 73–95 | Toluene | 140 min feed: tol/MAn and $iC_4$ | 10/4.5/0 | Filtration to toluene wet cake. Drying to powder | 50.0 | Powder neutralization to 50% TS | 2.0/3.0 |
| 11 | Semi-commercial scale distillation. Thin film evaporation | BPO | 0.5 | 75–96 | Toluene | 140 min feed: tol/MAn and $iC_4$ | 10/4.5/0 | Batch toluene/water distillation | 50.0 | Vacuum thin film evaporation | 2.0/3.0 |
| 12 | Semi-commercial scale drying to powder and neutralized to syrup | BPO | 0.5 | 73–89 | Toluene | 140 min feed: tol/MAn and $iC_4$ | 10/4.5/0 | Filtration to toluene wet cake. Drying to powder | 50.0 | Powder neutralization to 50% TS | 2.0/3.0 |
| 13 | Semi-commercial scale direct neutralization to syrup | BPO | 0.5 | 76–90 | Toluene | 140 min feed: tol/MAn and $iC_4$ | 10/4.5/0 | Filtration to toluene wet cake. Stripping/neutralization | 50.0 | Neutralization to 50% TS | 2.0/3.0 |
| 14 | Commercial scale reaction | BPO | 0.5 | 82–83 | Toluene | 140 min feed: tol $iC_4$ molten | 50/22/ | Batch tol/water distillation | 48.2 | Vacuum (thin film) evaporation | 2.0/3.0 |

TABLE 4-continued

| Ex No | Demonstration Type | A | B | C | Solvent Type | Polymer- isation Process Type | D | Solvent Removal Process | E | Concentration Process | F |
|---|---|---|---|---|---|---|---|---|---|---|---|
| | Conventional distillation Thin film evaporation | | | | | MAn | 2 | | | | |
| 15 | Commercial scale toluene distillation by steam injection/stripping | BPO | 0.2 | 79–83 | Toluene | 140 min feed: tol iC$_4$, molten MAn | 33/ 22/ 2 | Batch tol/water distillation | 47.0 | Vacuum (thin film) evaporation | 2.0/ 3.0 |
| 16 | Conventional distillation and thin film evaporation. | BPO | 0.3 | 79–83 | Toluene | 140 min feed: tol iC$_4$, molten MAn | 33/ 22/ 2 | Direct steam injection/stripping to 38% | 47.0 | Vacuum (thin film) evaporation | 2.0/ 3.0 |

A: Initiator type
B: Initiator Concentration (% mass on maleic anhydride total)
C: Reaction temperature (° C.)
D: Seeding (BPO/iC$_4$/MAn in % total charge)
E: Degree of Neutralization (% of theoretical carboxyl total)
F: Crosslinker addition (BDO/glycerol in % of copolymer before neutralization)

EXAMPLES 17 TO 19

Experiments were carried out to illustrate the control over particle size that can be afforded by means of the fifth aspect of the present invention. The details of the mental procedures and the results obtained are set out in Table 5.

TABLE 5

| Example No. | Ini- tiator Type | Reaction Tempera- ture | Feed Time (min) | Seeding as % of Charge (BPO/MAn/iC$^4$) | Particle Size By Laser Granulometry (median μm) |
|---|---|---|---|---|---|
| 17 | BPO | 81–82 | 140 | 50/2.2/12.5 | 6 |
| 18 | BPO | 80–82 | 100 | 50/2.2/14 | 12 |
| 19 | BPO | 78–80 | 50 | 50/2.2/12.5 | 112 |

It will be understood that the present invention has been described above purely by way of example, and modifications of detail can be made within the scope of the invention.

Each feature disclosed in the description, and (where appropriate) the claims and drawings may be provided independently or in any appropriate combination.

What is claimed is:

1. A process for producing a copolymer of an α,β-unsaturated monomer having at least one pendant unit selected from a carboxylic acid group and derivatives thereof, and a copolymerisable monomer wherein said copolymer has a peak molecular weight of greater than or equal to 5000 and said process comprises (a) copolymerising said monomers by free radical polymerisation involving the use of an initiator;
   (b) carrying out the copolymerisation in a reaction zone in a single aromatic solvent in which solvent the monomers and initiator are soluble and the copolymer is insoluble;
   (c) supplying the monomers separately to the reaction zone; and
   (d) controlling the addition rate of the monomers to the reaction zone.

2. A process according to claim 1, wherein the aromatic solvent is benzene or a substituted benzene.

3. A process according to claim 1, wherein the aromatic solvent is toluene.

4. A process according to claim 1, characterised in that the unsaturated monomer contains carboxylic acid anhydride groups.

5. A process according to claim 1, characterized in that the unsaturated monomer is maleic anhydride.

6. A process according to claim 1, characterized in that the copolymerisable monomer is selected from isobutylene and styrene.

* * * * *